United States Patent [19]

Mezei et al.

[11] Patent Number: 4,478,744

[45] Date of Patent: Oct. 23, 1984

[54] METHOD OF OBTAINING ANTIBODIES

[75] Inventors: Louis M. Mezei, Fremont; Jung S. Chen, Foster City; John J. Huang, San Mateo; Robert E. Lovins, Novato, all of Calif.

[73] Assignee: Sherwood Medical Company, St. Louis, Mo.

[21] Appl. No.: 342,418

[22] Filed: Jan. 25, 1982

[51] Int. Cl.$^3$ .................... C07C 103/52; C07G 7/00; A61K 39/00; A61K 37/00

[52] U.S. Cl. ........................ 260/112.5 R; 260/112 R; 424/85; 424/88; 424/177

[58] Field of Search .................... 260/112.5 R, 112 R; 424/177, 88, 85

[56] References Cited

PUBLICATIONS

Chou, et al., "Development of a Laser Nephelometric Method for the Quantitation of Human Glycohemoblogins", Analytical Letters, vol. 14 (B13) at 1071–1087, (1981).

Merrifield, R. B., "Solid Phase Peptide Synthesis, I, The Synthesis of a Tetrapeptide", JACS, vol. 85, p. 2149, (1963).

Javid, et al., British Journal of Haematology, vol. 38 at 329–337, (1978).

Brownlee, et al., Science, vol. 206, pp. 1190–1191, 1979.

Dixon, "A Reaction of Glucose with Peptides", Biochem. J., vol. 129, pp. 203–208, (1972).

Goodfriend, et al., "Antibodies to Bradykinin and Angiotensin: A Use of Carbodiimides in Immunology", Science, vol. 144, pp. 1344–1346, (1964).

Primary Examiner—Delbert R. Phillips
Attorney, Agent, or Firm—Stanley N. Garber; Gregory E. Upchurch; William R. O'Meara

[57] ABSTRACT

Antibodies specific to glycosylated hemoglobin and substantially free of cross-reactivity with non-glycosylated forms of hemoglobin are obtained by administering a synthetic antigen to a host animal. The antigen comprises a glycosylated synthetic peptide having an amino acid sequence corresponding to that of the NH$_2$-terminus of the $\beta$-chain of hemoglobin. The peptide comprises a sequence of between about four and ten, and preferably seven, amino acids, and is conjugated with glucose and a protein. The protein preferably comprises an immunoglobulin which is foreign to the host animal.

6 Claims, 2 Drawing Figures

METHOD OF OBTAINING ANTIBODIES

BACKGROUND OF THE INVENTION

1. Field of the Invention

This invention relates to a method of obtaining antibodies and, more specifically, this invention relates to a method of obtaining an antibody which is highly specific to glycosylated hemoglobin and substantially free of cross-reactivity with non-glycosylated forms of hemoglobin.

2. Description of the Prior Art

Many antigenic molecules which are clinically important are not subject to determination by immunoassay due to their molecular structure. Specifically, some antigens comprise large molecules having many antigenic sites and, as a result, antibodies produced from such antigens may exhibit a high degree of cross-reactivity with respect to various species of antigens, and thus are of only limited utility in immunoassay techniques.

Hemoglobin A1c (HbAlc) has an amino acid structure which is identical to that of the HbAo form of hemoglobin, except for the presence of a glucose moiety attached to the $NH_2$-terminus valine in the $\beta$-chain. The transformation of HbAo to HbAlc is a continuous process which is a function of blood glucose concentration. The level of HbAlc in a blood sample is an indication of an individual's carbohydrate metabolism.

Normal adults have about 90% of their total hemoglobin as HbAo, 2–3% as HbAla and HbAlb, and 3–6% of their total hemoglobin as HbAlc. However, the level of HbAlc in juvenile and maturity onset diabetics ranges from about 6% to about 15%. The level of HbAlc in hypoglycemic patients is correspondingly less than about 3%.

The quantification of the HbAlc level in diabetic patients is a useful means of assessing carbohydrate tolerance as well as adequacy of control. One prior method of determining the HbAlc level in a serum sample is the well-known column chromotography method wherein the sample is eluted through a column. Glycosylated hemoglobin is eluted prior to nonglycosylated hemoglobin.

However, the results of prior art column chromotography methods are sensitive to many variables, specifically including temperature, column length and ionic strength effects encountered in the column. Prior column methods require pre-separation steps, are not homogeneous, and are relatively nonspecific because they measure HbAo, HbAla, HbAlb, and HbF in addition to HbAlc.

Prior methods of producing antibodies to glycosylated hemoglobin for use in immunoassay procedures involve separation of glycosylated hemoglobin from serum, and production of antibodies by injection of the glycosylated hemoglobin fraction into a host animal. Resulting antibodies are then harvested and labeled, as with a radioactive label, and utilized in suitable assay methodologies, such as RIA.

Exemplary of such prior methods is the work of Cerami and co-workers described in U.S. Pat. No. 4,247,533 (Jan. 27, 1981) and in Javid et al, "Immunologic Characterization and Qualification of Haemoglobin A$_{lc}$", *British Journal of Haemotology*, Vol. 38 at 329–337 (1978).

Such prior assay methods have generally been unsuccessful, since the hemoglobin molecule is very large, having many antigenic sites, with only minor structural differences between glycosylated and nonglycosylated hemoglobin. Hence, prior assay methodologies have generally been characterized by low specificity due to cross-reactivity of antibodies produced by injection of HbAlc with various forms of nonglycosylated hemoglobin. See Chou et al, "Development of a Laser Nephelometric Method for the Quantitation of Human Glycohemoglobins", *Analytical Letters*, Vol. 14 (B13) at 1071–1087 (1981).

SUMMARY OF THE INVENTION

It is an object of the invention to overcome one or more of the problems described above.

According to the invention, antibodies which are highly specific to a selected antigen are obtained by immunization of a host animal with a synthetic analog of the antigen coupled to a carrier protein.

The antigenic analog is prepared by synthesizing an amino acid sequence corresponding to that of a portion of the antigen and of sufficient length to elicit an authentic immune response when administered to the host, yet insufficient to elicit production of antibodies which exhibit cross-reactivity to species other than the selected antigen.

Prior to immunization of the host, the synthetic amino acid sequence is coupled to a carrier protein, preferably through a covalent linkage.

More specifically, antibodies against glycosylated hemoglobin (specifically HbAlc) which are as substantially free of cross-reactivity to nonglycosylated hemoglobins (specifically, hemoglobins other than HbAlc) are obtained by synthesis of a suitable peptide, glycosylation and coupling of the peptide to a carrier protein, administration of the resulting synthetic antigen to a host animal, and harvesting of the resulting antiserum from the animal.

In a preferred embodiment, the antigen is prepared by first synthesizing a hapten consiting of a peptide having an amino acid sequence corresponding to the $NH_2$-terminus of the hemoglobin $\beta$-chain. The hapten comprises a sequence of between about four and ten, and preferably seven, of the amino acids which comprise the $NH_2$-terminus of the hemoglobin $\beta$-chain.

After synthesis, the peptide is glycosylated, preferably with a d-glucose, and conjugated, preferably by covalent linkage, with a suitable carrier protein.

After preparation, the glycosylated peptide-protein antigen is administered to a suitable host animal, and the resulting antiserum is harvested.

The protein is preferably an immunoglobulin which is foreign to the host animal, and the animal is preferably one whose metabolism does not naturally produce HbAlc. For example, the protein may be bovine IgG, and the host animal may be a sheep.

The resulting antibodies to the synthetic antigens are highly specific against HbAlc and thus may be used in any of various forms of immunoassay, including RIA, ELISA or EMIT immunoassay methodology, for example.

Thus, the invention also provides a method of quantitatively detecting the presence of HbAlc in a sample. This method is especially suitable for use in assessing carbohydrate intolerance in a living mammal.

A diagnostic test kit embodying the inventive antibodies, in combination with a suitable labeled antigen control, is also described.

DETAILED DESCRIPTION OF THE INVENTION

Figure 2:
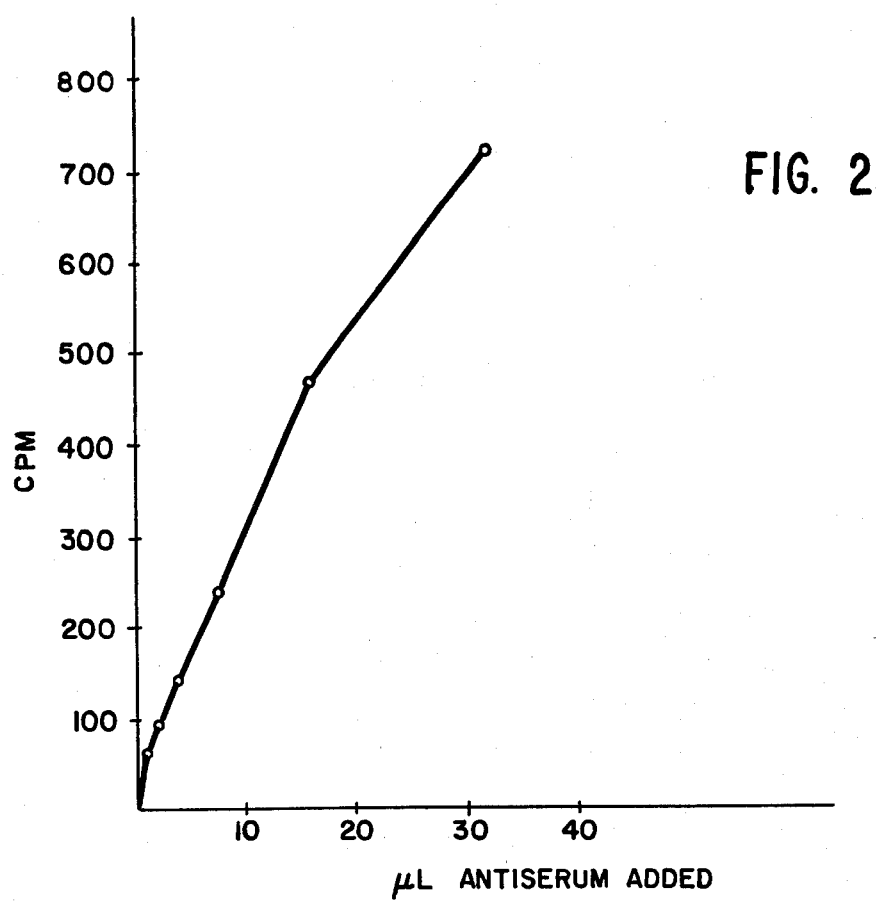

The method of the invention will be illustrated by reference to a specific application of the method to production of antibodies which are highly specific to HbAlc. It is to be understood, however, that the invention is not limited by reference to a specific application but is intended to apply to production of antibodies which are respectively highly specific to a wide variety of antigens.

Glycosylation of hemoglobin in both humans and animals occurs at the $NH_2$-terminus of the human hemoglobin β-chain of the hemoglobin molecule. The $NH_2$-terminus of the human hemoglobin β-chain is characterized by a specific amino acid sequence, as follows:

NH2—Val—His—Leu—Thr—Pro—Glu—
Glu—Lys—Ser—Ala—

The invention contemplates the chemical synthesis of a peptide consisting of a sequence of amino acids corresponding to that of all or a portion of the foregoing hemoglobin β-chain $NH_2$-terminal end. The peptide comprises between about four and ten, and preferably seven, of the foregoing amino acids in the sequence given.

After synthesis, the peptide is glycosylated at the terminal valine, which corresponds to the $NH_2$-terminus of the hemoglobin β-chain and is conjugated, preferably by means of a covalent linkage, with a suitable carrier protein, such as an immunoglobulin. The peptide may be glycosylated prior or subsequent to conjugation.

When administered to a host animal, the glycosylated and conjugated peptide promotes the formation of antibodies which, when harvested, may be utilized in immunoassay techniques for the quantitative and qualitative determination of glycosylated hemoglobin in a sample. The antibodies to the synthetic antigen are highly specific against HbAlc and are substantially free of cross-reactivity against other forms of hemoglobin.

The highly-specific hemoglobin Alc antibodies may be incorporated in a diagnostic test kit in either lyophilized or solution form, as described below.

Synthesis of Peptide

One disadvantage of utilizing pure hemoglobin Alc as an antigen to promote antibody production is that the hemoglobin Alc molecule is quite large and comprises many antigenic sites. In connection with this invention, a synthetic peptide having an amino acid sequence corresponding to that of the $NH_2$-terminus of the hemoglobin Alc β-chain is utilized, thus minimizing or substantially eliminating the production of antibodies which are nonspecific to hemoglobin Alc.

The synthesis of peptides comprising various selected sequences of amino acids is well known. One peptide synthesis method especially suitable for use in connection with this invention is described in Merrifield, R. B., "Solid Phase Peptide Synthesis.I.The Synthesis of a Tetrapeptide", *JACS* Vol. 85 p. 2149 (1963), the disclosure of which is hereby incorporated by reference. Numerous modifications of the Merrifield method have been published and are suitable for use in connection with this invention.

In this connection, an amino sequence of suitable length is prepared, preferably according to the procedure of Merrifield, above. Peptides comprising between about four and ten amino acids in the sequence of the hemoglobin β-chain $NH_2$-terminus are suitable for use in promoting antibody production. A peptide having a sequence of seven amino acids is preferred.

Thus, the synthetic peptide used in this invention has the following amino acid sequence:

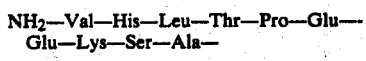

where Y is chosen from the group consisting of Thr—, Thr—Pro—, Thr—Pro—Glu—, Thr—Pro—Glu—Glu—, Thr—Pro—Glu—Glu—Lys—, Thr—Pro—Glu—Glu—Lys—Ser—, and Thr—Pro—Glu—Glu—Lys—Ser—Ala—. Preferably, the peptide is a sequence of seven amino acids, and the Y component comprises Thr—Pro—Glu—Glu—.

A suitable synthetic peptide having a desired amino acid sequence, and prepared according to the Merrifield procedure can be obtained from Peninsula Laboratories, P.O. Box 1111, San Carlos, Calif., 94070 (USA).

Example 1, below, illustrates the Merrifield procedure for preparing the preferred peptide of this invention.

Glycosylation of Peptide

The synthetic peptide prepared according to the foregoing is glycosylated by addition of glucose, preferably d-glucose, to the terminal valine thereof.

Several methods for carrying out such glycosylation are known. One such method is described by Brownlee et al, "A Glucose-Controlled Insulin Delivery System: Semisynthetic Insulin Bound to Lectin", *Science*, Vol. 206, pp. 1190-1191 (1979), the disclosure of which is hereby incorporated by reference. The Brownlee et al glycosylation method comprises simple incubation of d-glucose and a peptide in a 0.1 M $NaPO_4$ buffer, pH=8.0, at 37° C. for a reaction period of up to about ten days.

A preferred method of glycosylating a synthetic peptide is described in Dixon, "A Reaction of Glucose with Peptides", *Biochem. J.*, Vol. 129, pp. 203-208 (1972), the disclosure of which is hereby incorporated by reference.

According to the Dixon method a 1:1 (v/v) mixture of pyridine and glacial acetic acid is added to a mixture of peptide and d-glucose in a suitable container. The reaction mixture is stirred at ambient temperature for a suitable period of time, typically several days.

After reacting, the mixture is placed in a freeze-dryer and solvent is evaporated to dryness. The resulting almost dry material may be refined as set forth in Example 2, below.

The glycosylated peptide may be characterized by silica gel thin layer chromatography, or by other suitable characterization methods, in order to assure that the desired glycosylated peptide is obtained.

Glycosylation of peptide according to the Dixon method has been found to result in at least about 95% glycosylation of the peptide. The Brownlee et al method, on the other hand, while useful, typically results only in about 50% glycosylation.

Conjugation of Glycosylated Peptide with Protein

In accordance with the invention, and before or after glycosylation, the peptide prepared as described above is conjugated at its Y-terminus with a carrier protein such that, when the conjugated peptide is administered to a host animal, the conjugated peptide acts as an antigen to promote the production of antibodies which are subject to harvesting.

Any of a wide variety of proteins may be used as a carrier for the peptide. It is preferred, however, that the protein be one which is foreign to the host animal.

For example, if the host animal is a sheep, a suitable protein is one which as been derived from a cow, or another suitable animal other than a sheep.

The protein carrier is preferably a relatively large molecule, such as bovine albumin, rabbit albumin, alkaline phosphatase, or others, in order to enhance the antigenic capability of the conjugated peptide. A preferred type of protein carrier is immunoglobulin-G, preferably bovine IgG when the host animal is a sheep.

The glycosylated peptide is linked to the carrier at the peptide Y-terminus by any of a variety of methods. The peptide is preferably covalently linked with the protein.

One preferred method of conjugating a peptide with a protein is described in Goodfriend et al., "Antibodies to Bradykinin and Angiotensin: A Use of Carbodiimides in Immunology", *Science*, Vol. 144, pp. 1344–1346 (1964), the disclosure of which is hereby incorporated by reference.

While the Goodfriend et al article describes a method of covalently linking a peptide to a protein with a carbodiimide linkage, it is to be understood that other types of linkages may be used. Suitable linking agents including glutaraldehydes, N-N-carbonyldiimidazole, 1-hydroxybenzotriazole monohydrate, N-hydroxy succinimide, n-trifluoroacetylimidazole, or cyanagen bromide.

Briefly stated, the Goodfriend et al method involves a reaction between a protein such as bovine IgG, a peptide and a carbodiimide, such as 1-ethyl-3-(3-dimethyl-aminopropyl) carbodiimide hydrochloride ("Ethyl CDI") in water at ambient temperature. A reaction production in the form of a precipitate and a colloidal suspension is obtained. The reaction mixture is dialyzed against distilled water at low temperatures and, after dialysis, the reaction mixture may be lyophilized, or used in solution form.

Production of Antibodies

The antigen obtained as described is administered to a host animal, such as a goat, sheep, etc. by any suitable method and resulting antibodies are harvested. Usually, an adjuvant, preferably Freund's complete or incomplete adjuvant, is administered with the antigen to promote antibody production.

The host animal is preferably one whose metabolism does not naturally produce hemoglobin Alc.

Immunoassay Utilizing HbAlc-Specific Antibodies

The antibodies obtained as described above are highly specific to HbAlc, and are useful in any of a wide variety of immunoassay techniques, including RIA, enzyme immunoassay techniques such as ELISA and EMIT systems, and fluorescent immunoassay techniques.

The HbAlc-specific antibodies are conveniently incorporated into a diagnostic test kit wherein the antibodies are packaged in a container, either in lyophilized or solution form, with a separate container containing radioactive or enzyme-labeled hemoglobin Alc antigen control material. The control material may comprise antigen produced according to the invention.

The following specific examples are given for purposes of illustration, and are to be considered preferred forms of the invention. However, no unnecessary limitations are to be inferred from the examples, as obvious variations in procedure and constituents will be obvious to those skilled in the art.

Example 1—Preparation of Synthetic Peptide

A synthetic peptide having the following sequence:

Val—His—Leu—Thr—Pro—Glu—Glu— is prepared according to the method of Merrifield, above, using an automatic Schwarz/Mann synthesizer, as follows:

Boc—Glu(OBzl)-resin (1 mM/2 g of resin) is used as the solid support. The following Boc-protected amino acids are successively added to the Boc—Glu—(OBzl)-resin: Glu(OBzl), Pro, Thr(Bzl), Leu, His(Tos) and Val. A 3.0 molar excess of each protected amino acid is used. The success of the coupling reaction is monitored by the semi-quantitative ninhydrin test.

The following steps are used to couple each Boc-amino acid to the Boc—Glu(OBzl)-resin:

1. washing with $CH_2Cl_2$ (1×50 ml)
2. prewashing with 35% $CF_3COOH$ in $CH_2Cl_2$ (1×50 ml)
3. deprotection with 35% $CF_3COOH$ in $CH_2Cl_2$ (1×50 ml, 20 min)
4. washing with $CH_2Cl_2$ (2×50 ml)
5. washing with EtOH (1×50 ml)
6. washing with $CH_2Cl_2$ (2×50 ml)
7. prewashing with 10% $Et_3N$ in $CH_2Cl_2$ (1×50 ml)
8. neutralization with 10% $Et_3N$ in $CH_2Cl_2$ (1×50 ml), 10 min.)
9. washing with $CH_2Cl_2$ (3×50 ml)
10. protected amino acid (3.0 molar excess) in $CH_2Cl_2$ (50 ml) is added
11. DCC in $CH_2Cl_2$ (0.5 M, 6 ml) is added (the reaction time is up to 2 hr.)
12. washing with $CH_2Cl_2$ (3×50 ml)

The resulting protected heptapeptide, Boc—Val—His(Tos)—Leu—Thr(Bzl)—Pro—Glu(OBzl)-resin is washed well with 35% $CF_3COOH$ in $CH_2Cl_2$, $CH_2Cl_2$ and MeOH respectively. After drying in vacuo overnight, the peptide resin is cleaved by HF (30 ml) in the presence of anisole (10 ml) for one hour at 0° C. The reaction mixture is dried in vacuo and washed with anhydrous ether. The desired heptapeptide is dissolved in 10% HOAc and the resin is filtered off. The filtrate is lyophilized to give crude Val—His—Leu—Thr—Pro—Glu—Glu.

This peptide is purified by counter-current distribution using n-BuOH:HOAc:$H_2O$ (4:1:5 v/v) as the partition solvent, affording pure Val—His—Leu—Thr—Pro—Glu—Glu (450 mg).

Characterization of the peptide is carried out as follows:

Thin-layer chromatography: $R_f$ 0.28 (silica gel plate; n-BuOH:HOAc:EtOAc:H$_2$O ratio of 1:1:1:1; ninhydrin spray) and $R_f$ 0.24 (silica gel plate; n—BuOH:Pyridine:HOAc:H$_2$O ratio of 15:10:3:12; ninhydrin spray).

Electrophoresis: Whatman 3 MM paper, pH 5.6 pyridine-acetate buffer, 1000 V, one hour. $R_f$ 0.16 with reference to picric acid.

Amino acid anlaysis: 6 N HCl at 110° C. for 72 hours. His 0.98, Thr 0.92, Glu 2.10, Pro 1.00, Leu 1.03 and Val 0.97.

Example 2—Glycosylation of Peptide

The peptide of Example 1 is glycosylated with d-glucose according to the method of Dixon et al., above, as follows:

16.4288 mg of the peptide of Example 1, in the form of a lyophilized, fluffy white light powder (MW 821.44) and 5.50 mg of anhydrous d-glucose (C$_6$H$_{12}$O$_6$ Mallinkrodt, Inc. Product No. 4912, Lot No. WAPR, MW 180.16) are introduced to a 4 ml glass vial. 1 ml of a 1:1 (v/v) mixture of pyridine and glacial acetic acid is added to the glass vial to slowly dissolve the contents. The contents are then stirred magnetically at room temperature for 144 hours.

The reaction mixture is then placed in a freeze-dryer for about 26 hours and dried in vacuo to result in a brown colored, sticky material which is nearly dry. This material was dissolved in 1.5 ml methanol and then precipitated slowly by addition of anhydrous diethyl ether. The mixture was maintained at 4° C. overnight.

The precipitate was then collected by centrifugation (400 rpm, 4° C.) in glass tubes. The supernatant liquids were pipetted off and the precipitates were initially dried under a thin stream of nitrogen, then full dried under vacuum for 4 hours. The dried material was dissolved in 2 ml distilled water and then lyophilized.

The lyophilized material was characterized by paper electrophoresis using Pauly reagent as a glycosylated peptide having the following structure:

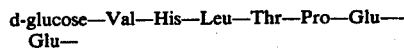

It was found that over 95% of the peptide introduced to the reaction was glycosylated. A minor product was a double glycosylated form of the peptide having the following probable structure:

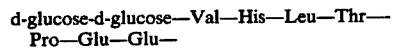

Example 3—Conjugation of Glycosylated Peptide with Bovine Gamma Globulin

The glycosylated peptide of Example 2 is conjugated with bovine IgG according to the procedure of Goodfriend et al, above, as follows:

Approximately 14 mg of bovine gamma globulin (Sigma No. G-3500, Lot No. 89C-0063-1) and 28 mg of the glycosylated peptide of Example 2 were dissolved together in 0.75 ml of distilled water.

To this mixture was added 0.4 ml of distilled water containing 250 mg of freshly dissolved 1-ethyl-3-(3-dimethylaminopropyl) carbodiimide hydrochloride ("Ethyl CDI") (Sigma No. E-7750, Lot No. 69C-0297). The reaction was permitted to proceed with gentle rotation for 60 minutes. The pH as checked with pH paper was between 6 and 8.

Formation of a precipitate and a colloidal suspension was noted. The entire reaction mixture was dialyzed for 24 hours against distilled water at 4° C. with five changes of water (1 liter of distilled water was added at each change).

After 24 hours of dialysis, the entire reaction mixture was transferred to glass vials and lyophilized over a 3-day period. The resulting product is a dry, light and fluffy brown powder weighing 17 mg.

The conjugation reaction is preferably carried out at a pH of between about 3 and 8, but a pH outside of the range is acceptable, although the yield may be lower. A pH of about 7 is preferred.

The reaction may be carried out at a wide range of temperatures (e.g. 2° C.-56° C.), but room temperature or below is preferred. 4° C. is especially preferred.

The mole ratio of peptide to carrier protein is widely variable, and depends primarily on the number of binding sites present on the protein molecule.

Example 4—Immunization of Host Animal

Two sheep were obtained through Tago, Inc. of Burlingame, Calif. Non-immuned serum is obtained from each sheep before immunization.

5.0 mg of the glycosylated, conjugated peptide (antigen) of Example 3 is dissolved in 6 mL of saline(0.9%) solution, and 6 mL of Freund's Complete Adjuvant is added to form an emulsion. Each sheep is immunized by intradermal injection at 12 sites using a total of 6 mL emulsion (2.5 mg antigen) per sheep.

Booster injections are carried out 21 days, 34 days, and 62 days following the initial inoculations. For the first booster injection, an emulsion comprising 4.0 mg of the antigen of Example 3, 6.0 mL of 0.9% saline solution, and 6.0 mL of Freund's Incomplete Adjuvant is used. Each sheep is injected intradermally with a total of 6.0 mL of the emulsion at at least 10 sites.

For the second booster injection, an emulsion comprising 4.0 mg of the antigen, 5.0 mL of 0.9% saline solution, and 5.0 mL of Freund's Incomplete Adjuvant is used. Each sheep is injected intradermally with a total of 4.0 mL of the emulsion at at least 10 sites.

The emulsion used in the third booster injection comprises 3.0 mg of the antigen, 5.0 mL of 0.9% saline solution and 5.0 mL of Freund's Incomplete Adjuvant. Each sheep is injected intradermally with a total of 5.0 mL of the emulsion at at least 10 sites.

Example 5—Detection of Antibodies to HbA1c

A test bleeding of the sheep of Example 4 is carried out 61 days after the initial immunization (1 day prior to the third booster injection), and a sample of blood subjected to the well-known Ouchterlony Double Diffusion Technique to detect the presence of antiserum to HbA1c. (The testing was carried out at room temperature for 72 hours, using pure HbA1c (1mg/mL in 0.9% saline) and pure HbAo (1 mg/mL in 0.9% saline). The diffusion plates are then rinsed with 0.9% saline (with three changes) for 72 hours, and rinsed with distilled water (with three changes) for one day. The plates are then dried at 56° C. overnight and stained.)

The results clearly indicate the presence of antibodies to HbA1c.

The antibodies obtained as described above are identified as being highly specific to HbA1c, and are useful in effecting immunoassay of HbA1c in any of a variety of body fluids according to any convenient immunoassay technique.

The antiserum obtained as described above is highly specific to HbAlc, as demonstrated by the following Examples 6 and 7.

Example 6—Radioactive Labeling of Antigen

Radioactive labeled indexed antigen (HbAlc) is prepared by the well-known Chloramine T procedure, as follows:

Sephadex is swelled in 0.01 M PBS at room temperature overnight, and a column is packed in a 10 ml disposible pipette (gel bed volume=about 10 ml). The column and bed are then washed with 50 ml PBS, and the column is equilibrated with 20 ml of an elution buffer.

(The elution buffer solution comprises 0.01 M sodium phosphate buffer (pH 7.5), 0.15 M NaCl, 0.25% (w/v) bovine serum albumin, 0.01% (w/v) EDTA (disodium salt), and 0.01% (w/v) NaN$_3$.)

The concentration of substantially pure HbAlc in 0.01 M sodium phosphate buffer (pH 7.5) is adjusted to 1 μg/μL, and 5 μL (5 μg) of the resulting solution is introduced to a Pierce Reacti-Vial ® reaction vial. 25 μL of 0.5 M sodium phosphate buffer (pH 7.5) is added, along with 1 mci NaI-125. 5 μL chloramine T is added, and the vial is capped and gently mixed.

The reaction is allowed to proceed for about 15 seconds, and 25 μL sodium metabisulfite solution (6.3 mg in 10 mL 0.05 M sodium phosphate buffer (pH 7.5)) is added to stop the reaction.

The reaction mixture is applied to the Sephadex column, and the vial is rinsed with 50 μL of elution buffer solution. The elution buffer is then carefully applied to the column, and the flow rate adjusted to 10 seconds/drop.

Figure 1:
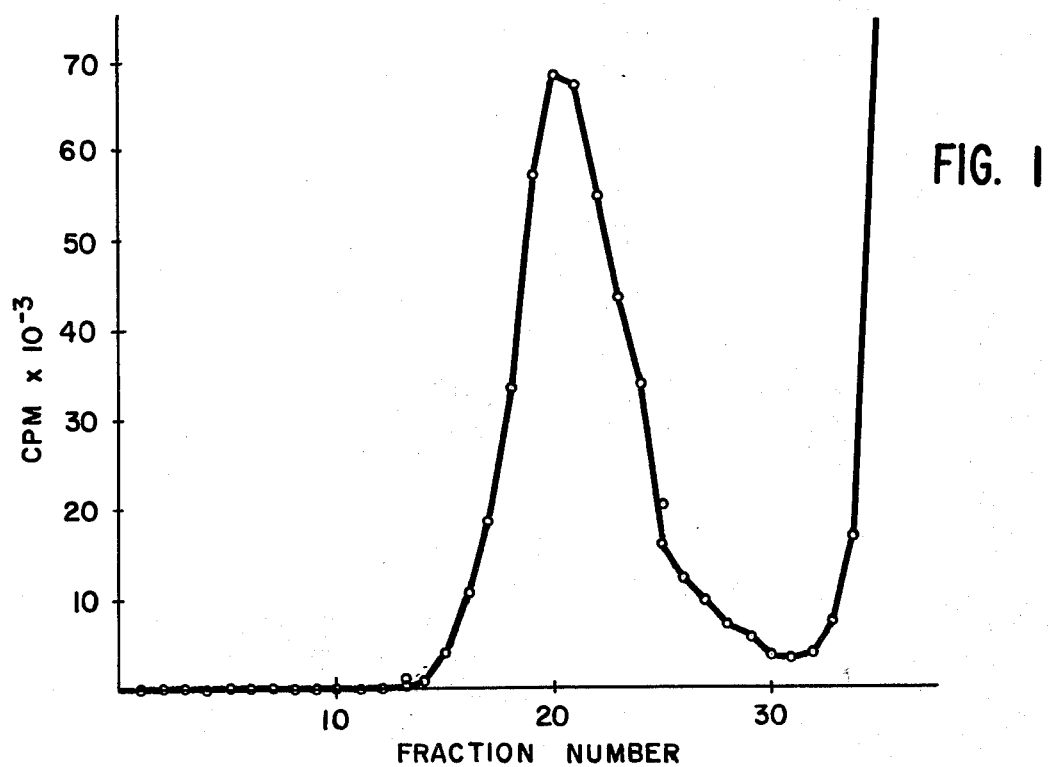
FIG. 1 is an elution profile of the iodinated antigen (HbAlc) fractions produced in Example 6; and, FIG. 2 is a curve of an antibody titer of antiserum produced according to the invention.

A total of 40 fractions (10 drops/fraction) are collected and 1 μL from each fraction is taken for readioactive counting to obtain an elution profile, shown in FIG. 1.

As can be clearly seen in FIG. 1, iodinated antigen fractions are separate from fractions containing free iodine.

The fractions containing iodinated HbAlc are then pooled, and are suitable for dilution or concentration, depending upon the intended use of the labeled HbAlc.

(The quality of the labeled HbAlc can be quickly checked by precipitating aliquots thereof with trichloroacetic acid (5%), and counting the radioactivity of the precipitate and supernatant liquid, respectively. Normally, over 90% of the radioactivity will be precipitatd; otherwise, the quality of the labeled HbAlc should be regarded as poor).

Example 7—Assay of Antibody Titer

The $^{125}$I-labeled HbAlc of Example 6 is diluted in a dilution buffer solution which comprises 0.01 M sodium phosphate buffer (pH 7.5), 0.15 M NaCl, 1 mM EDTA (disodium salt), 0.1% (w/v) NaN$_3$, and 2% (w/v) bovine serum albumin. The activity of the diluted labeled antigen is about 20–30 KCPM/200 μL.

Rabbit anti(sheep IgG) is diluted in the dilution buffer at 1:200. Polyethylene glycol is added to a total of 6%.

Antiserum obtained in Examples 4 and 5 is diluted (in series) in normal sheep serum (serum obtained from the sheep of Example 4 prior to the initial immunization).

200 μL of dilute HbAlc solution is placed in each of a series of test tubes, and 100 μL of each antiserum dilution, each containing between zero and 31 μL, is added to the tubes. (e.g. 100 μL of a dilution containing 20 μL of antiserum contains 80 μL normal sheep serum.)

The tubes are incubated at room temperature for 12–16 hours, and 0.7 mL of the rabbit anti(sheep IgG) dilution is added to each tube. The tubes are then vortex-mixed, incubated at room temperature for 15 minutes, centrifuged and the supernatant liquids decanted.

The radioactivity of the precipitate in each tube is counted in a γ counter, using normal sheep serum as the blank. Results are shown in FIG. 2.

FIG. 2 clearly shows that an increase in antiserum concentration results in an increase in antigen (HbAlc) precipitation, thus demonstrating that the antiserum of the invention reacts with the glycosylated N-terminal end of the HbAlc antigen.

Further, the antiserum can be demonstrated to be substantially free of cross-reactivity to forms of hemoglobin other than HbAlc, as by the well-known RIA dilution technique, using "cold" (unlabeled) HbAlc, HbAo, etc.

Immunoassay for HbAlc

The highly specific antibodies of the invention, obtained as described above, may be used for quantitatively detecting the presence of HbAlc in a blood sample by any of various suitable immunoassay techniques, including RIA, EIA and fluorescent immunoassay.

In such an assay, substantially pure HbAlc comprises the index antigen, which can be labeled radioactively (e.g. as with iodine-125, as shown in Example 6, above), or with an enzyme capable of quantitative detection, or with a fluorescein label.

In a preferred embodiment of RIA, a sample is reacted with an antibody made according to the invention which is highly specific against HbAlc but which is substantially free of cross-reactivity against the human hemoglobin Ao, Ala and Alb, to produce an antibody-antigen (i.e. antibody-HbAlc) complex. The presence of the complex is then quantitatively determined by radio-immunoassay by reacting the complex with radioactive labeled HbAlc, or with labeled antigen of the invention.

The reactions between the labeled HbAlc and the antibody-HbAlc complex can conveniently be carried out at room temperature to about 37° C., for about one-half hour.

The foregoing immunoassay methods, specifically including the RIA method detailed above, are useful in assessing carbohydrate intolerance in a living mammal. In such an assessment, the presence of HbAlc in a sample of the mammal's blood is quantitatively determined. Levels in excess of about 6% are indicative of carbohydrate intolerance.

Diagnostic kits for quantitatively assessing HbAlc levels in a sample may comprise a container of the inventive antibody, in combination with a labeled (e.g. radioactively labeled) amount of substantially pure HbAlc for use as an antigen control. Labeling is preferably with iodine-125. The antibody may be packaged in either solution form, or lyophilized form suitable for reconstitution. Labeled antigen of the invention can alternatively be used as the control.

The foregoing detailed description is given for clearness of understanding only, and no unnecessary limitations are to be inferred therefrom, as modifications will be obvious to those skilled in the art.

We claim:

1. A method of preparing an antigen useful in obtaining antibodies against HbAlc, which antibodies are substantially free of cross-reactivity to nonglycosylated hemoglobin, said method comprising the steps of:
(a) synthesizing a hapten consisting of a peptide having the formula Val—His—Leu—Y wherein Y is chosen from the group consisting of Thr—, Thr—Pro—, Thr—Pro—Glu—, Thr—Pro—Glu—Glu—, Thr—Pro—Glu—Glu—Lys—, Thr—Pro—Glu—Glu—Lys—Ser—, and Thr—Pro—Glu—Glu—Lys—Ser—Ala—, said hapten thereby having an amino acid sequence corresponding to the $NH_2$ terminus of the hemoglobin $\beta$-chain;
(b) reacting the peptide of step (a) with glucose to obtain a glycosylated peptide having the formula glucose—Val—His—Leu—Y;

and
(c) conjugating the glycosylated peptide of step (b) with a protein to form an antigen suitable for injection into a host animal whose metabolism does not naturally produce HbAlC for production of antibodies thereto.

2. The method of claim 1 wherein said protein is an immunoglobulin.

3. The method of claim 2 wherein said protein comprises IgG.

4. The method of claim 1 wherein said peptide is covalently linked to said protein.

5. The method of claim 4 wherein said peptide is conjugated to said protein through a carbodiimide linkage.

6. The method of claim 2 wherein said peptide comprises d-glucose—Val—His—Leu—Thr—Pro—Glu—Glu—, said protein is bovine IgG, and said peptide is covalently linked to said bovine IgG through a carbodiimide linkage.

* * * * *